(12) United States Patent
Hlavinka et al.

(10) Patent No.: US 9,079,194 B2
(45) Date of Patent: Jul. 14, 2015

(54) CENTRIFUGE FOR PROCESSING BLOOD AND BLOOD COMPONENTS

(75) Inventors: Dennis J. Hlavinka, Arvada, CO (US); John R. Merkling, Lakewood, CO (US)

(73) Assignee: Terumo BCT, Inc., Lakewood, CO (US)

( * ) Notice: Subject to any disclaimer, the term of this patent is extended or adjusted under 35 U.S.C. 154(b) by 1030 days.

(21) Appl. No.: 13/185,256

(22) Filed: Jul. 18, 2011

(65) Prior Publication Data

US 2012/0015795 A1 Jan. 19, 2012

Related U.S. Application Data

(60) Provisional application No. 61/365,602, filed on Jul. 19, 2010.

(51) Int. Cl.
*B04B 5/04* (2006.01)
*B04B 7/12* (2006.01)
*A61M 1/36* (2006.01)

(52) U.S. Cl.
CPC ............ *B04B 5/0428* (2013.01); *A61M 1/3693* (2013.01); *B04B 7/12* (2013.01); *A61M 2202/0427* (2013.01)

(58) Field of Classification Search
CPC ............. B04B 5/0428; A61M 1/3693; A61M 2202/0427
USPC ................................ 494/37, 43, 45
See application file for complete search history.

(56) References Cited

U.S. PATENT DOCUMENTS

| | | | |
|---|---|---|---|
| 3,096,283 | A | 7/1963 | Hein |
| 3,145,713 | A | 8/1964 | Latham, Jr. |
| 3,244,363 | A | 4/1966 | Hein |
| 3,297,244 | A | 1/1967 | Hein |
| 3,326,458 | A | 6/1967 | Meryman et al. |
| 3,456,875 | A | 7/1969 | Hein |
| 3,489,145 | A | 1/1970 | Judson et al. |
| 3,519,201 | A | 7/1970 | Eisel et al. |
| 3,600,900 | A | 8/1971 | Buddecke |
| 3,679,128 | A | 7/1972 | Unger et al. |
| 3,708,110 | A | 1/1973 | Unger et al. |
| 3,724,747 | A | 4/1973 | Unger et al. |
| 3,737,096 | A | 6/1973 | Jones et al. |

(Continued)

FOREIGN PATENT DOCUMENTS

| | | |
|---|---|---|
| DE | 3815645 A1 | 11/1989 |
| EP | 0304431 B1 | 6/1993 |

(Continued)

OTHER PUBLICATIONS

PCT/US2011/044391, "International Search Report", mailed Nov. 22, 2011.

(Continued)

*Primary Examiner* — Timothy Cleveland
(74) *Attorney, Agent, or Firm* — René A. Pereyra

(57) ABSTRACT

The present invention relates generally to the field of extracorporeal blood processing methods and apparatus which are particularly useful in blood component collection, and more specifically, the present invention relates to methods and apparatus for centrifugally separating buffy coat that reduce the surface available for separated buffy coat components to sediment on by varying the radius of the product collection bag.

16 Claims, 6 Drawing Sheets

(56) References Cited

U.S. PATENT DOCUMENTS

| | | |
|---|---|---|
| 3,858,796 A | 1/1975 | Unger et al. |
| 3,864,089 A | 2/1975 | Tiffany et al. |
| 3,885,735 A | 5/1975 | Westbert |
| 3,987,961 A | 10/1976 | Sinn et al. |
| 4,010,894 A | 3/1977 | Kellogg et al. |
| 4,111,355 A | 9/1978 | Ishimaru |
| 4,131,369 A | 12/1978 | Gordon et al. |
| 4,142,670 A | 3/1979 | Ishimaru et al. |
| 4,230,263 A | 10/1980 | Westberg |
| 4,244,513 A | 1/1981 | Fayer et al. |
| 4,268,393 A | 5/1981 | Persidsky et al. |
| 4,278,202 A | 7/1981 | Westberg |
| 4,303,193 A | 12/1981 | Latham, Jr. |
| 4,304,357 A | 12/1981 | Schoendorfer |
| 4,386,730 A | 6/1983 | Mulzet |
| 4,387,848 A | 6/1983 | Kellogg et al. |
| 4,389,206 A | 6/1983 | Bacehowski et al. |
| 4,389,207 A | 6/1983 | Bacehowski et al. |
| 4,405,079 A | 9/1983 | Schoendorfer |
| 4,419,089 A | 12/1983 | Kolobow et al. |
| 4,421,503 A | 12/1983 | Latham, Jr. et al. |
| 4,439,177 A | 3/1984 | Conway |
| 4,447,221 A | 5/1984 | Mulzet |
| 4,459,169 A | 7/1984 | Bacehowski et al. |
| 4,482,342 A | 11/1984 | Lueptow et al. |
| 4,530,691 A | 7/1985 | Brown |
| 4,617,009 A | 10/1986 | Ohlin et al. |
| 4,720,284 A | 1/1988 | McCarty |
| 4,767,397 A | 8/1988 | Hohenberg et al. |
| 4,846,780 A | 7/1989 | Galloway et al. |
| 4,850,952 A | 7/1989 | Figdor et al. |
| 4,925,442 A | 5/1990 | Bodelson |
| 4,934,995 A | 6/1990 | Cullis |
| 4,936,820 A | 6/1990 | Dennehey et al. |
| 4,940,543 A | 7/1990 | Brown et al. |
| 4,990,132 A | 2/1991 | Unger et al. |
| 5,032,288 A | 7/1991 | Columbus et al. |
| 5,114,396 A | 5/1992 | Unger et al. |
| 5,160,310 A | 11/1992 | Yhland |
| 5,217,426 A | 6/1993 | Bacehowski et al. |
| 5,217,427 A | 6/1993 | Cullis |
| 5,316,540 A | 5/1994 | McMannis et al. |
| 5,571,068 A | 11/1996 | Bacehowski et al. |
| 5,593,378 A | 1/1997 | Dyck |
| 5,610,074 A | 3/1997 | Beritashvili et al. |
| 5,651,766 A | 7/1997 | Kingsley et al. |
| 5,674,173 A | 10/1997 | Hlavinka et al. |
| 5,733,253 A | 3/1998 | Headley et al. |
| 5,759,147 A | 6/1998 | Bacehowski et al. |
| 5,789,259 A | 8/1998 | Wardlaw |
| 6,261,217 B1 | 7/2001 | Unger et al. |
| 6,296,602 B1 | 10/2001 | Headley |
| 6,315,706 B1 | 11/2001 | Unger et al. |
| 6,348,031 B1 | 2/2002 | Unger et al. |
| 6,656,105 B2 | 12/2003 | Hogberg et al. |
| 6,740,239 B2 | 5/2004 | Hogberg et al. |
| 7,819,793 B2 | 10/2010 | Menhennett et al. |
| 7,833,185 B2 | 11/2010 | Felt et al. |
| 2008/0053203 A1 | 3/2008 | Hogberg et al. |
| 2008/0220959 A1* | 9/2008 | Holmes et al. .................. 494/45 |
| 2009/0272701 A1 | 11/2009 | Holmes et al. |
| 2011/0077140 A1 | 3/2011 | Holmes et al. |

FOREIGN PATENT DOCUMENTS

| | | |
|---|---|---|
| EP | 0771569 B1 | 5/1997 |
| EP | 0578086 B1 | 8/2001 |
| EP | 1391244 A2 | 2/2004 |
| FR | 2593412 | 7/1987 |
| GB | 1373672 A | 11/1974 |
| SE | 354581 B | 3/1973 |
| SE | 354582 B | 3/1973 |
| WO | 85/02561 A1 | 6/1985 |
| WO | 87/06844 A1 | 11/1987 |
| WO | 87/06857 A1 | 11/1987 |
| WO | 92/00145 A1 | 1/1992 |
| WO | 94/25086 A1 | 11/1994 |
| WO | 95/01842 A1 | 1/1995 |
| WO | 95/04591 A1 | 2/1995 |
| WO | 96/29081 A1 | 9/1996 |
| WO | 98/35757 A1 | 8/1998 |
| WO | 98/46362 A1 | 10/1998 |
| WO | 01/02037 A1 | 1/2001 |
| WO | 01/97943 A1 | 12/2001 |
| WO | 03/089027 A2 | 10/2003 |
| WO | 2004/018021 A2 | 3/2004 |
| WO | 2005/030398 A2 | 4/2005 |
| WO | 2007/024550 A2 | 3/2007 |

OTHER PUBLICATIONS

PCT/US2011/044391, "Written Opinion", mailed Nov. 22, 2011.

Runck, A.H. et al., "Continuous-flow Centrifugation Washing of Red Blood Cells", Transfusion, Jul.-Aug. 1972, pp. 237-244, vol. 12, No. 4.

Contreras, T.J. et al., "A Comparison of Methods to Liquid-Stored Red Blood Cells and Red Blood Cells Frozen with High or Low Concentrations of Glycerol", Transfusion, Nov.-Dec. 1976, pp. 539-565, vol. 15, No. 6.

* cited by examiner

CENTRIFUGE FOR PROCESSING BLOOD AND BLOOD COMPONENTS

CROSS REFERENCE TO RELATED APPLICATIONS

This application claims the benefit of U.S. Provisional Application No. 61/365,602 filed Jul. 19, 2010.

FIELD OF THE INVENTION

The instant invention relates to a centrifuge for processing blood and blood components and for pooling buffy coat collections. This invention would be useful in any system with a central compartment where blood components are collected during centrifugation.

BACKGROUND OF THE INVENTION

Different types of centrifuges intended for processing blood and blood components and also several types of ring bags intended for use in these centrifuges are described in, for example, WO87/06857; U.S. Pat. No. 5,144,396; U.S. Pat. No. 5,732,050; WO97/30715; and WO98/35757. An apparatus for pooling buffy coat collections is described in U.S. Pat. No. 6,656,105. In the apparatus described in U.S. Pat. No. 6,656,105, the center well or central compartment or chamber to hold the platelet collection bag forms a cylindrical wall parallel to the axis of rotation of the centrifuge. This cylindrical wall provides a relatively large surface against which the platelets sediment under centrifugal force. This cylindrical wall also determines the sedimentation distance of the platelets.

SUMMARY OF THE INVENTION

It is an object of this instant invention to reduce the sedimentation surface against a wall available for platelets in a centrifuge. This, in turn, increases the distance through which platelets must sediment before settling onto the wall. The result is that most of the platelets remain suspended in plasma or Platelet Additive Solution (PAS) when they are removed from the central chamber. Platelets in suspension are of a better quality than platelets that have sedimented onto the wall.

This present invention includes a centrifuge for processing buffy coat, comprising a rotor with a central axis of rotation, a central chamber on the rotor capable of receiving a product collection bag, and a separation chamber capable of receiving a separation vessel containing buffy coat. The separation vessel is connected to the product collection bag where separated buffy coat components can pass from the separation chamber to the central chamber. The central chamber of the centrifuge has an inner wall with a varying radius from the central axis of rotation, an upper portion, and a lower portion. When the product collection bag is received in the central chamber, the bag extends adjacent to both the upper and lower portions of the inner wall.

Another aspect of the present invention is a system for processing buffy coat comprising a bag assembly, and a centrifuge for processing buffy coat components. The bag assembly includes a separation vessel, a product collection bag, and at least one conduit connecting the separation vessel to the product collection bag. The centrifuge for processing buffy coat comprises a rotor with a central axis of rotation; a central chamber on the rotor, wherein the product collection bag is in the central chamber; and a separation chamber capable of receiving the separation vessel containing buffy coat. The central chamber of the centrifuge has an inner wall with a varying radius from the central axis of rotation, an upper portion, and a lower portion. The product collection bag extends adjacent to both the upper and lower portions of the inner wall.

In one embodiment of the invention, the upper portion of the inner wall of the central chamber described above has a greater radius than any radius of the lower portion. In another embodiment of the invention, the lower portion has a greater radius than any radius of the upper portion. Also in one embodiment, the upper portion and/or the lower portion may have a constant radius with respect to the central axis of rotation. The inner wall may also have a middle portion that is between the upper and lower portions of the inner wall that may be sloped at an angle. The radius of the lower portion of the wall may decrease or increase from its top, defined by the middle portion, to its bottom, defined by the bottom of the central chamber. The radius with respect to the central axis of rotation of the upper portion may decrease or increase from its top, defined by the top of the central chamber, to its bottom, defined by the lower portion of the inner wall. In one embodiment of the present invention, the inner wall may comprise a removable insert for the central chamber.

In one embodiment of the invention, the separated component of the buffy coat is platelets. The separated platelets are passed to the product collection bag, wherein the inner wall of the central chamber is configured such that the platelets sediment out on either the upper portion of the inner wall or the lower portion of the inner wall.

Another aspect of the present invention includes a method for separating blood composites from buffy coat in a centrifuge. The centrifuge used in the method has a rotor with a central axis of rotation and a central chamber on the rotor, and the central chamber has an inner wall. The method includes loading a separation vessel onto the centrifuge, loading a product collection bag in the central chamber of the centrifuge, loading the separation vessel with buffy coat, rotating the centrifuge at a sufficient rate such that platelets separate from the buffy coat, collecting the separated platelets in the product collection bag, and reducing the surface area for the collected platelets to contact the product collection bag.

In one embodiment of the invention, the reducing step may comprise preventing platelets from contacting the entire inner wall. The preventing step may comprise varying the radius of the product collection bag with respect to the central axis of rotation. The varying step may comprise providing the inner wall with an upper and a lower portion, where the upper portion has a greater radius than the lower portion and where the product collection bag extends adjacent to both the upper and lower portions of the inner wall. The varying step may alternatively comprise providing the inner wall with a lower portion that has a greater radius than any radius of the upper portion of the inner wall, and extending the product collection bag adjacent to both the upper and lower portions of the inner wall.

In one embodiment of the invention, the reducing step may comprise shaping the product collection bag during the collecting step to conform the product collection bag to the inner wall of the central chamber. The shaping step may include varying the radius of the product collection bag with respect to the central axis of rotation. Additionally, the central chamber may have a top and a bottom and the reducing step may comprise decreasing or increasing the inner wall radius of the central chamber along the central axis of rotation from the top to the bottom, comprising providing the inner wall with an upper portion and a lower portion. In one embodiment of the invention, the upper portion may have a radius with respect to the central axis of rotation that is greater than any radius of the lower portion and the product collection bag extends adjacent to both the upper and lower portions of the inner wall. In another embodiment, the lower portion may have a radius with respect to the central axis of rotation that is greater than any radius of the upper portion and the product collection bag extends adjacent to both the upper and lower portions of the inner wall.

In one embodiment, the reducing step may also comprise adding an insert inside the central chamber to form the inner wall and to vary the radius of the central chamber between the central axis of rotation and the inner wall. The inner wall may be provided an upper and a lower portion where the product collection bag extends adjacent to both portions of the inner wall. The upper portion may have a greater radius than any radius of the lower portion with respect to the central axis of rotation. In another embodiment, the lower portion has a greater radius than any radius of the upper portion.

DETAILED DESCRIPTION OF THE INVENTION

Figure 1:
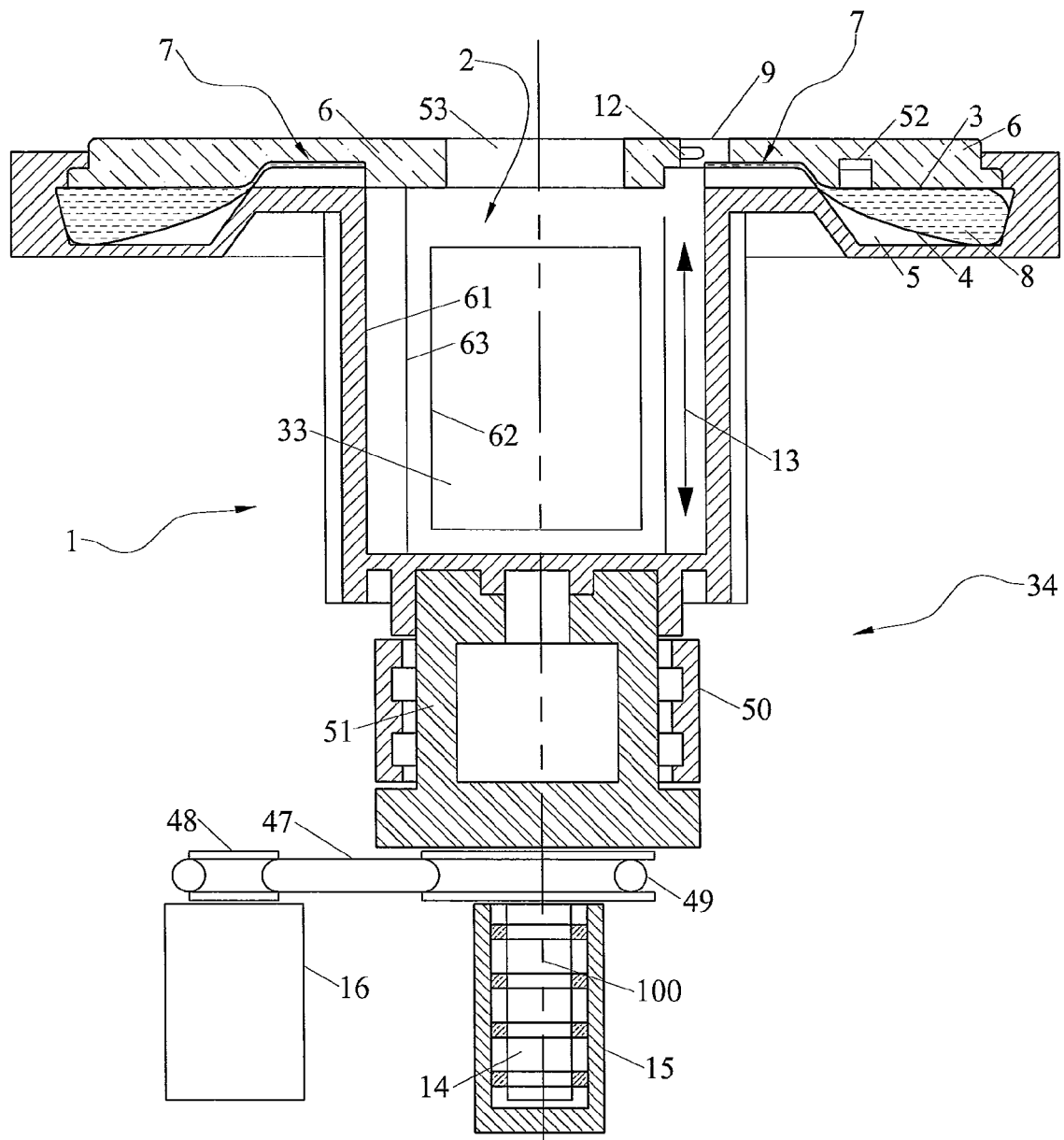
FIG. 1 illustrates a cross-sectional view through a typical centrifuge in accordance with the prior art.
Figure 9:
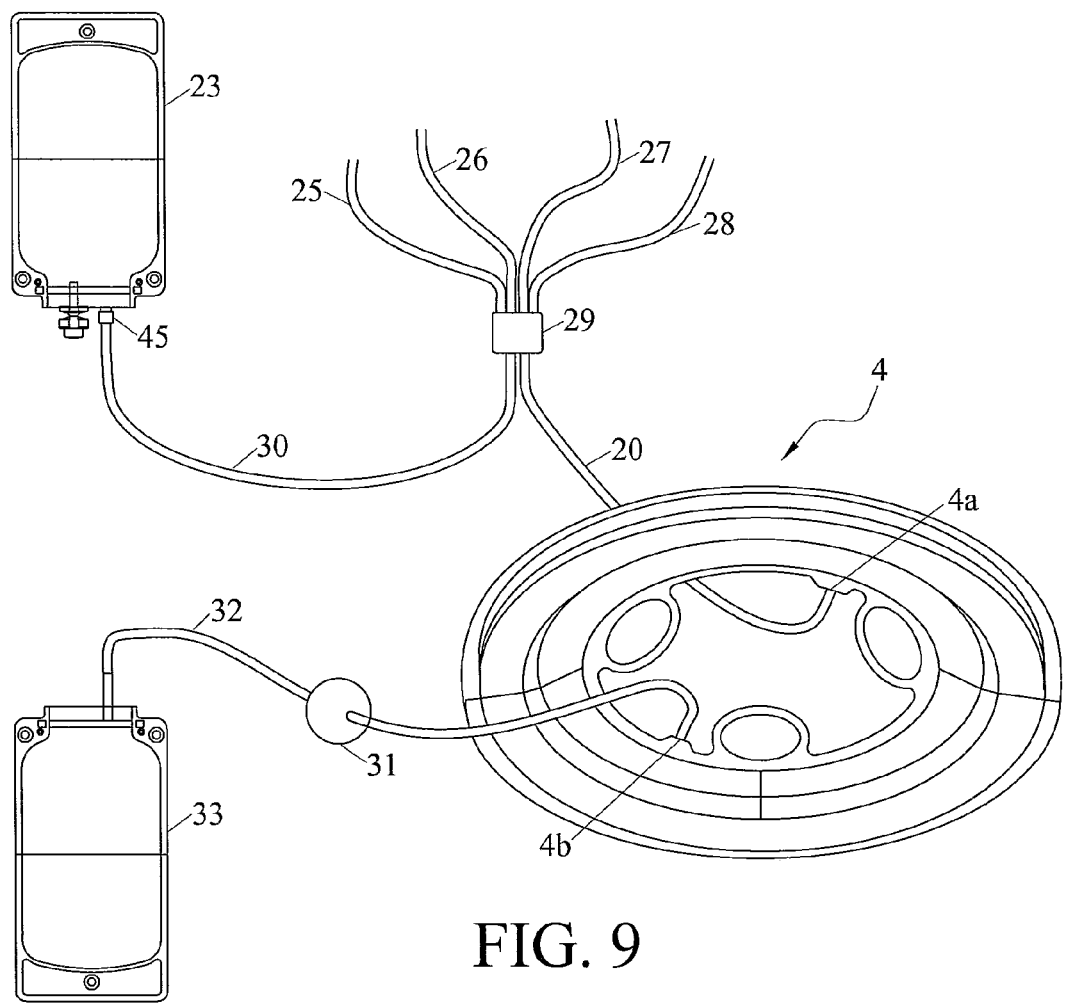
FIG. 9 is a schematic of a bag set intended for blood platelet production from buffy coat.

The centrifuge 34 shown in FIG. 1 has a rotor 1 with a central axis of rotation 100, and a central chamber 2, where, for example, the final storage, product collection or satellite bags for produced or collected separated products can be located during a centrifuging operation. The central chamber has an outer wall 61 and an inner wall 63. The satellite bags, such as bag 33 in FIG. 9, are connected to a ring or annularly-shaped separation vessel 4. Furthermore, a ring or separation chamber 3 is included on the rotor 1 to receive ring or separation vessel 4. In one embodiment of the present invention, the separation chamber 3 surrounds the central chamber 2. The area beneath the ring or separation vessel 4 in the separation chamber 3 forms a chamber 5. The chamber 5 can be filled with a hydraulic fluid with the purpose of applying pressure or squeezing the ring or separation vessel 4. Centrifuge rotor 1 further includes a rotating inner lid 6 which includes a securing portion 7 for the ring or separation vessel 4. A sensor for sensing component movement is included at 52.

In FIG. 1, ring or separation vessel 4 is shown filled with fluid 8 which is a composite fluid or composite buffy coat (as described below) for separation. There are three supports 9, 10, and 11 on the centrifuge rotor 1. Of these, only support 9 is shown in FIG. 1, but see also FIG. 8. The supports 9, 10, and 11 locate the position of ring or separation vessel 4 and also provide guide grooves 12, 21 and 22, respectively, to secure different connecting tubes or tubing or conduits between the separation vessel 4 and the satellite or product collection bags as well as a tube, tubing or conduits from the diluting fluid or buffy coat composite fluid bags as will be described below. Supports 9, 10, and 11 may be configured such that the guide grooves 12, 21 and 22 may be selectively reduced and/or increased in size to clamp or unclamp tubing or connecting tubes placed in the grooves. For example, a portion of the support 9 could be configured to move in the direction of arrow 13 so as to function as a clamp valve. Also, one or more of supports 9, 10, and 11 may be configured to provide a welding function, which, when activated, seals and cuts the tubes positioned in the guide grooves 12, 21 and 22.

The welding function on the supports requires access to electric power in the centrifuge rotor and may also receive commands from a control system of the centrifuge. Any electrical connection occurs through slip ring connectors between the rotor and centrifuge stand where 14 indicates the centrifuge's rotor portion and 15 indicates the centrifuge stand. On FIG. 1, the centrifuge motor is marked as 16. Motor 16 rotates the centrifuge rotor through driving belt 47; driving belt 47 is located between the motor's driving pulley 48 and the centrifuge's driving pulley 49. The centrifuge's rotation bearing is 50 and the centrifuge's rotating guide is 51. In the centrifuge's inner lid or cover 6, there is a central opening 53 which permits central chamber 2 to be accessible externally even when the inner lid or cover 6 is closed.

Figure 8:
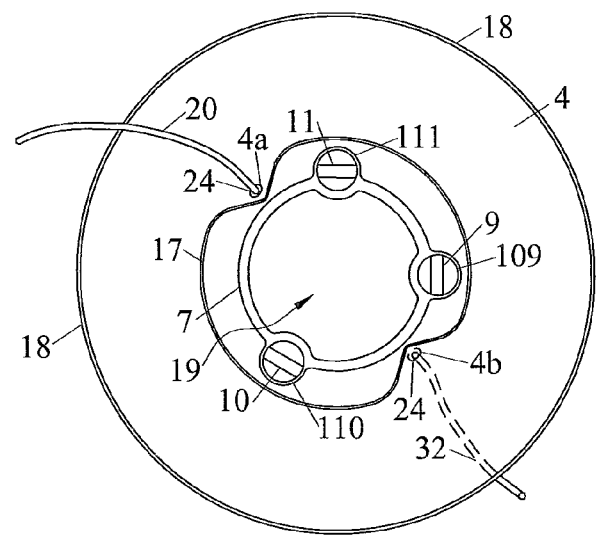
FIG. 8 is a top view of a ring or separation bag for the centrifuge of FIG. 1 or FIG. 5.

Ring or separation vessel 4, as shown in FIG. 8, comprises two sheets of suitable plastic material joined together along the welded edges 17 and 18. An external ring vessel for separation of a blood composite and buffy coat is formed between the welded edges 17 and 18. Besides ring welds 17 and 18, there are additional welded points for strengthening around the holes which are intended for locating ring or separation vessel 4 on supports 9, 10, and 11. All the ring or separation vessels shown in the Figures are formed with a central opening, where the central opening primarily corresponds to the center chamber 2 opening when the separation vessel 4 is in the centrifuge 34. In FIG. 8, this opening is designated 19. The ring or separation vessel 4 shown in FIG. 8 has openings 109, 110, and 111 for supports 9, 10, and 11, respectively. Input tube 20 and output tube 32 are attached to the ring or the separation vessel's top and bottom sides by means of the welded sleeve couplings 24. Ports with flat securing collars 4a and 4b can be welded to the ring or separation vessel's top and bottom sides in which the connecting tubes 20 and 32 are secured by welding. Instead of being secured via the port and securing collar, the input tube 20 and output tube 32 can also be secured to each respective welded edge, i.e., welding 17 and welding 18 in FIG. 8.

FIG. 9 shows the bag set for collecting blood platelets from buffy coat. This bag set includes ring or separation vessel 4, a bag with diluting solution 23, four connecting tubes or conduits 25, 26, 27, and 28 (the number of connecting or separation tubes can vary with the number of buffy coat collections, but generally the number is between four and six). In use, each tube 25, 26, 27, and 28 can be connected such as by welding or sterile connection to bags with buffy coat, such as bags 37, 38, 39, 40 in FIG. 10. A multi-way connector 29 is connected to the diluting solution bag 23 via a tube or conduit 30. Tube 20 is further connected to the tubes 25, 26, 27, and 28 through the multi-way connector 29. Tube 32 is connected from the ring or separation vessel 4 to a final storage, product collection, or satellite bag 33. A leukoreduction filter 31 may also be included. Tube 30, which extends from diluting solution bag 23 to multi-way connector 29, is arranged in the guide groove 22 in support 11 to provide a clamp valve function for control of the addition of diluting solution. Bag 23 may also contain an optional openable closer or frangible closer at 45.

Figure 10:
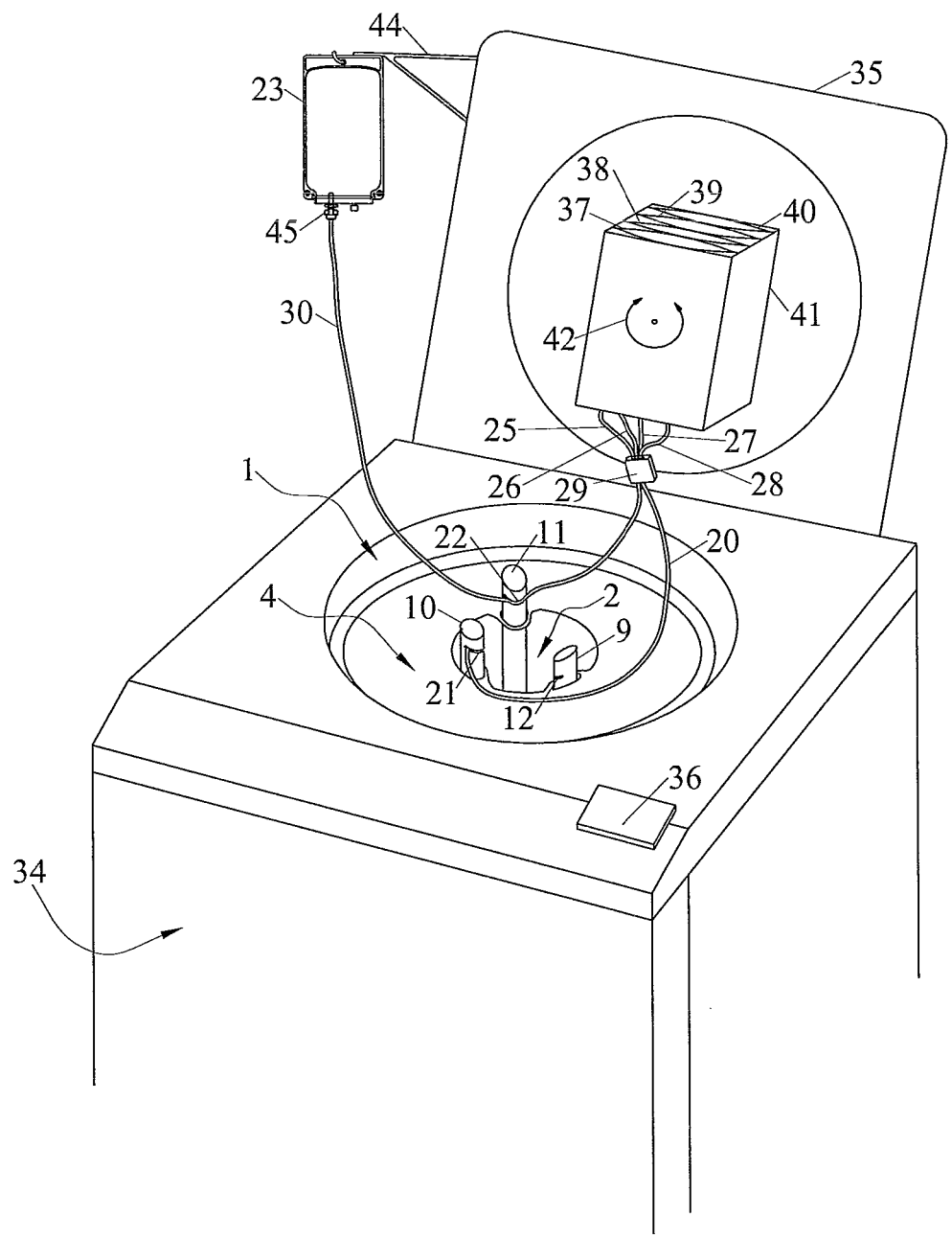
FIG. 10 is a schematic view of a centrifuge equipped with buffy coat pooling.

The bag set shown in FIGS. 8 and 9 is used in the apparatuses of FIG. 2, 3, 4, 5, 6 or 7, and, in FIG. 10, for buffy coat pooling. In FIG. 10, the centrifuge 34 is shown with an outer lid 35 open and locked in position. The centrifuge's inner lid 6 has been omitted in this figure, but see FIG. 7. Also, the centrifuge rotor 1 and the ring or separation vessel 4 are drawn in a simplified manner. The centrifuge's control panel is shown schematically at 36. Furthermore, a cassette 41 mounted on the inside of the centrifuge's outer lid 35 and rotatable as shown at 42, holds blood bags 37, 38, 39, and 40 which contain buffy coat. Bag 23, containing a diluting solution, is mounted via holder 44 at a level vertically higher than bags 37, 38, 39, 40.

Figure 7:
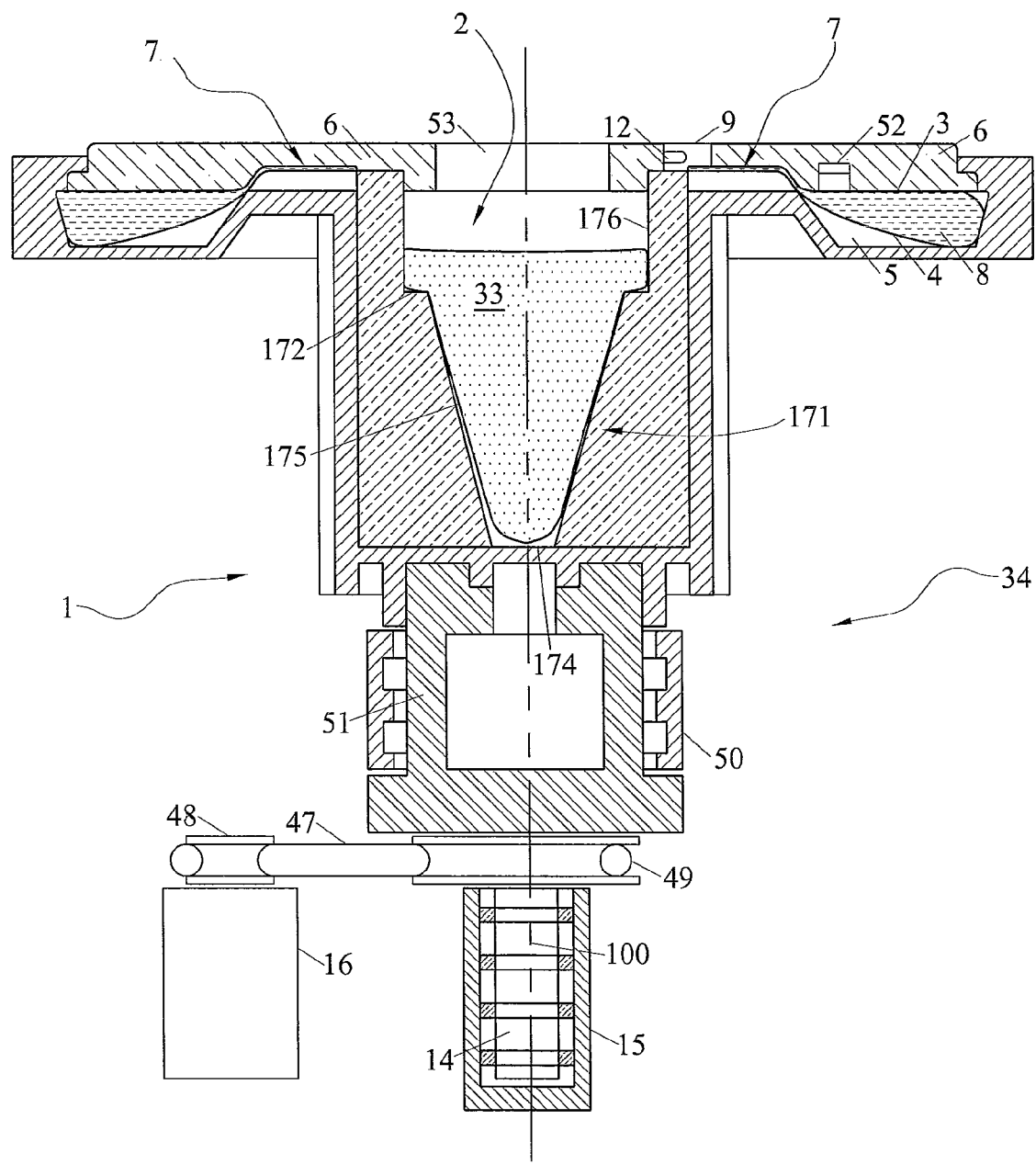
FIG. 7 is a cross-sectional view of a centrifuge with a central chamber wall in accordance with the invention.

As shown in FIG. 7, in operation, when the bag set of FIG. 9 is loaded on the centrifuge rotor 1, final storage, product collection or satellite bag 33 is placed in the central chamber 2. In the prior art FIG. 1, the sides 62 of the bag 33 are generally parallel to the outer wall 61 and the inner wall 63 of the central chamber.

Figure 2:
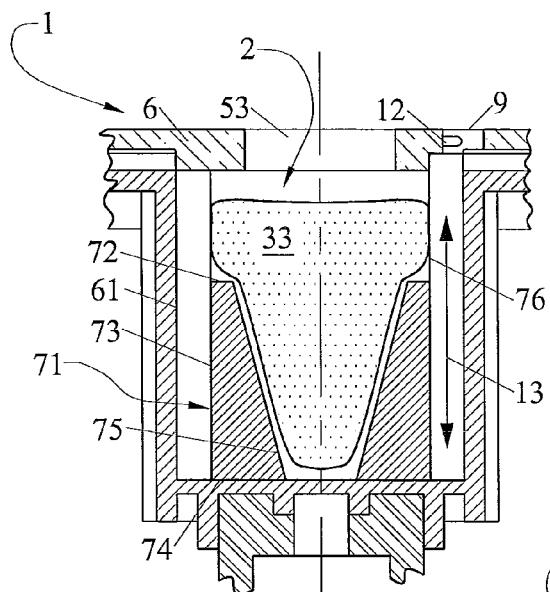
FIG. 2 illustrates a cross-sectional view of an alternate central chamber in accordance with the invention for the centrifuge of FIG. 1.

In FIG. 2, a removable insert 71 is provided for central chamber 2 to vary the radius of the inner wall of central chamber 2 with respect to the central axis of rotation 100. The insert 71 includes a top side 72, an outer side 73, a bottom 74, and a sloping inner side 75. The insert 71 has a height between the top side 72 and bottom side 74 that is less than the height of the central chamber 2. The top side of the insert 72 defines a middle portion of the inner wall of the central chamber 2. The sloping inner side 75 of the insert 71 defines a lower portion of the inner wall of the central chamber 2. The lower portion 75 of the inner wall has a radius with respect to the central axis of rotation 100 that decreases from its top, defined by the middle portion 72, to its bottom, defined by the bottom of the insert 74. The portion of the inner wall 76 above the insert 71 defines an upper portion of the inner wall of the central chamber 2. The insert 71 fits inside the central chamber 2 to shape product collection bag 33 during centrifugation as is more fully described below.

Figure 3:
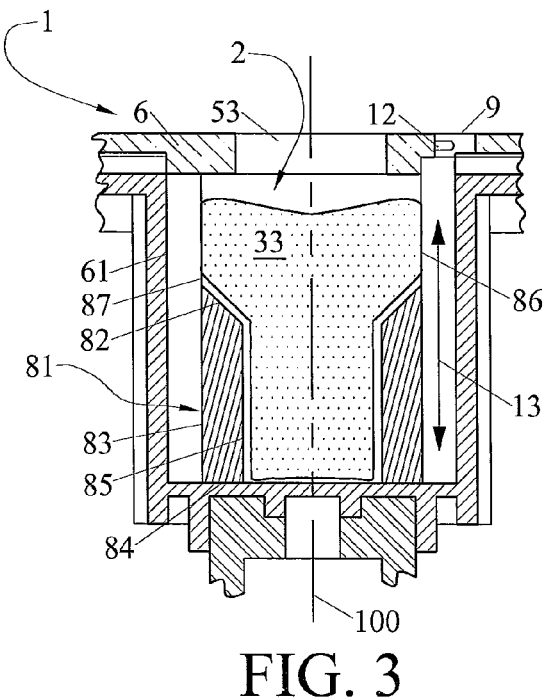
FIG. 3 illustrates a cross-sectional view of an alternate central chamber in accordance with the invention for the centrifuge of FIG. 1.

FIG. 3 illustrates an alternative removable insert 81 with a sloping top side 82, inner and outer sides 85 and 83, and a bottom 84. This insert also has a height between the highest point 87 of top side 82 and bottom 84 that is less than the overall height of the central chamber 2. The inner side 85 defines a lower portion of the inner wall of the central chamber, and the sloping top side 82 of the insert defines a middle portion of the inner wall of the central chamber. The middle portion 82 is sloped at an angle greater than 0 degrees and less than or equal to 90 degrees with respect to the outer wall of the central chamber 61. The portion 86 of the central chamber above the insert 81 defines an upper portion of the inner wall of the central chamber 2. Both the upper portion 86 and lower portion 85 of the inner wall have constant radii with respect to the central axis of rotation 100.

Figure 4:
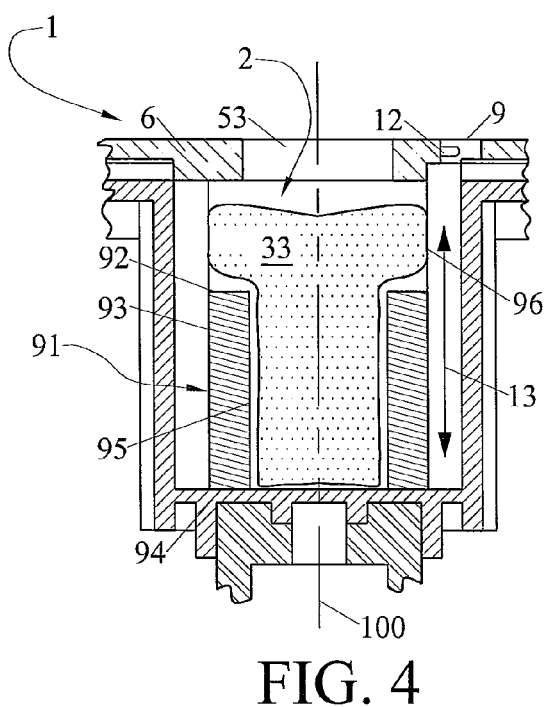
FIG. 4 illustrates a cross-sectional view of an alternate central chamber in accordance with the invention for the centrifuge of FIG. 1.

A third alternative removable insert 91 is shown in FIG. 4. This insert has parallel top side 92 and bottom 94. An outer side 93 is parallel to an inner side 95. The insert 91 has a height between the top side 92 and the bottom side 94 that is less than the overall height of the central chamber 2. The portion 96 of the central chamber above the insert 91 defines an upper portion of the inner wall of the central chamber 2. The inner side 95 defines a lower portion of the inner wall, and the top side 92 of the insert 91 defines a middle portion of the inner wall of the central chamber 2. Both the upper portion 96 and lower portion 95 of the inner wall have constant radii with respect to the central axis of rotation 100.

Figure 5:
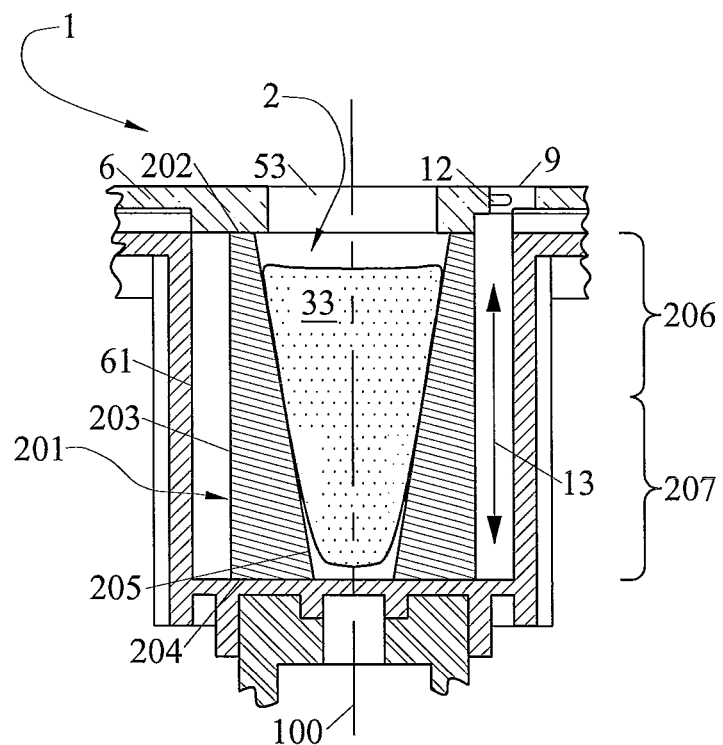
FIG. 5 illustrates a cross-sectional view of an alternate central chamber in accordance with the invention for the centrifuge of FIG. 1.

A fourth alternative removable insert 201 is shown in FIG. 5. The insert 201 has a bottom 204, an outer side 203, an inner side 205, and a top side 202. The insert 201 extends the length of central chamber 2 from central chamber 2's opening to its bottom. The inner side 205 of the insert 201 defines an inner wall of the central chamber 2. The inner wall 205 is divided into portions. The portion 206 of the inner wall 205 defines an upper portion of the inner wall of the central chamber 2. The portion 207 of the inner wall 205 defines a lower portion of the inner wall 205 of the central chamber 2. Both the upper portion 206 and the lower portion 207 of the inner wall have decreasing radii with respect to the central axis of rotation 100 from the top of the central chamber 2 to the bottom of the central chamber 2.

Figure 6:
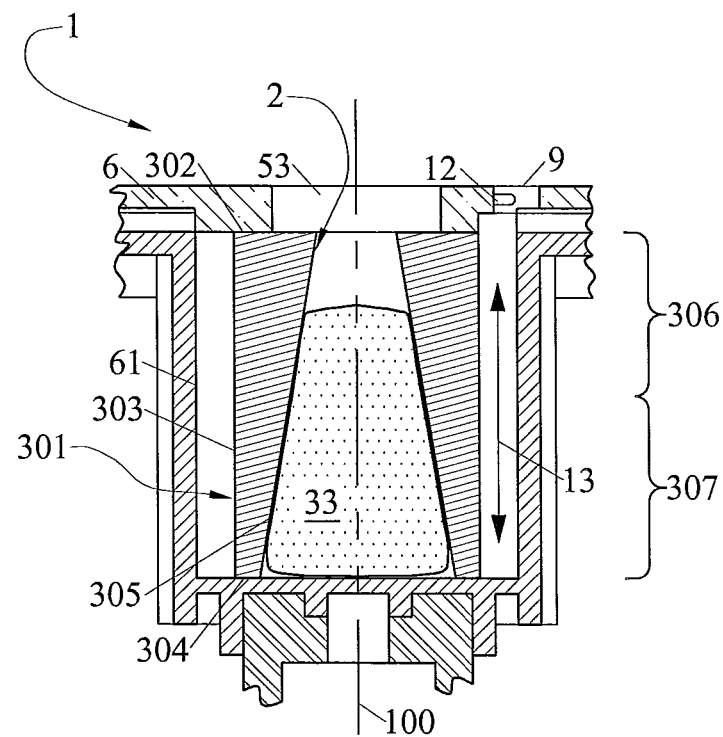
FIG. 6 illustrates a cross-sectional view of an alternate central chamber in accordance with the invention for the centrifuge of FIG. 1.

A fifth alternative removable insert 301 is shown in FIG. 6. The insert 301 has a bottom 304, an outer side 303, an inner side 305, and a top side 302. The insert 301 extends the length of central chamber 2 from central chamber 2's opening to its bottom. The inner side 305 of the insert 301 defines an inner wall of the central chamber 2. The inner wall 305 is divided into portions. The portion 306 of the inner wall 305 defines an upper portion of the inner wall of the central chamber 2. The portion 307 of the inner wall 305 defines a lower portion of the inner wall 305 of central chamber 2. Both the upper portion 306 and the lower portion 307 of the inner wall have increasing radii with respect to the central axis of rotation 100 from the top of the central chamber 2 to the bottom of the central chamber 2.

As described, the inserts 71, 81, 91, 201 and 301 fit inside the central chamber 2 permitting the central chamber 2 to have an inner wall with a varied radius, shaping the product collection bag 33 during centrifugation. The product collection bag 33, when received, is positioned in the central chamber 2 adjacent to both the upper portions 76, 86, 96, 206, 306 and the lower portions 75, 85, 95, 207, 307 of the inner wall of the central chamber 2. The upper portions 76, 86, 96, 206 of the inner wall have a radius greater than any radius of the lower portions 75, 85, 95, 207 of the inner wall with respect to the central axis of rotation 100. However, the upper portion may have a greater radius than the lower portion of the inner wall such as in FIG. 6 and still accomplish the goal of reducing the surface area for platelets to sediment on. An insert consistent with such a configuration is shown in FIG. 6; insert 301 has a lower portion 307 of the inner wall 305 with a radius with respect to the central axis of rotation 100 greater than any radius of the upper portion 306 of the inner wall 305. In the case that the upper portion of the inner wall has a greater radius than the lower portion of the inner wall, then the middle portion of the inner wall will be sloped at an angle greater than or equal to 90 degrees and less than or equal to 180 degrees with respect to the outer wall of the central chamber.

FIGS. 2, 3, 4, 5, and 6 describe removable inserts. However, as shown in FIG. 7, the central chamber inner wall 171 can be manufactured having a varied radius without an insert. As shown in FIG. 7, the upper portion 176 of the inner wall has a constant radius from the central axis of rotation 100 greater than any radius of the lower portion 175 of the inner wall. A middle portion 172 divides the upper portion 176 of the inner wall from the lower portion 175 of the inner wall. A bottom of the lower portion of the inner wall is shown at 174. As shown in FIG. 7, under centrifugal forces, a portion of product collection bag 33 extends adjacent to both the lower portion 175 of the inner wall and the upper portion of the inner wall 176.

Although only a wall configuration similar to FIG. 2 is shown in FIG. 7, it is understood that wall configurations similar to FIGS. 3, 4, 5, and 6 could be used to define the inner wall of the central chamber 2 rather than using an insert.

Before the buffy coat is separated into its components, the buffy coat in bags 37, 38, 39, 40 must be loaded into the separation vessel 4. As ring or separation vessel 4 is loaded on the centrifuge rotor 1, the product collection bag 33 is loaded into the central chamber 2 for product collection. Also, tube or conduit 30 is placed in groove 22 in support 11, tube or conduit 20 is placed in groove 21 in support 10 and tube or conduit 32 is placed in groove 12 in support 9. To begin the process of transferring or loading the buffy coat into the ring or separation vessel 4, a small amount of diluting solution will be flowed through tube 30 after opening the valve in support 11 and optional frangible 45, through multi-way connector 29, and through tubes 25, 26, 27, 28 into bags 37, 38, 39, 40, respectively. After the addition of diluting solution in sufficient amounts to bags 37, 38, 39, 40, a motor operatively connected to cassette 41 is actuated to oscillate cassette 41 forward and backwards in a pendulum movement, shown as 42, until all remaining concentrate substance in the buffy coat bags 37, 38, 39, 40 is suspended in the diluting solution. After sufficient agitation for suspension, the valve in support 10 on the rotor is opened through which tubing 20 passes from the multi-way connector 29 to drain or load the buffy coat into separation vessel 4. The process of adding diluting solution to bags 37, 38, 39, 40, agitating, and draining the mixture of buffy coat and diluting solution through multi-way connector 29 and into tube 20 can be repeated until there is no remaining buffy coat in bags 37, 38, 39, 40. The buffy coat and diluting solution flow through tube 20 to ring or separation vessel 4.

After the buffy coat and diluting solution have been drained or loaded into ring or separation vessel 4, tubes 20 and 30 can be cut and sealed in guide grooves 21 and 22, respectively, by the welding function in supports 10 and 11. Cassette 41, holder 44, bags 37, 38, 39, 40 and 23, and all associated tubing are removed from the centrifuge lid whereby the centrifuge is closed for the centrifugation operation.

The rotor 34 is rotated at 1800 rpm or at a sufficient rpm that the less dense platelets separate from the denser Red Blood Cells (RBC) and leukocytes of the buffy coat. The built-in valve in guide groove 12 in support 9 can be opened and separation vessel 4 can be squeezed using the hydraulic fluid in chamber 5 to permit the less dense platelets and any plasma or diluting solution to be transferred through tube 32 to product collection bag 33 to be collected. While being expressed or passed from the separation vessel 4 to the product collection bag 33, the platelets can be pushed through the optional filter 31, shown on FIG. 9, and collected into the product collection bag 33. The transfer of the platelets and any plasma continues until a sensor 52 indicates the interface between the platelets and RBCs/leukocytes. After the final expression of platelets, tube 32 is sealed by sterile welding using the welding function on support 9. The platelets in bag 33 will continue to be subjected to centrifugal force until the centrifuge slows to a stop.

During centrifugation, the surface area is reduced for the collected platelets to contact the product collection bag and platelets are prevented from contacting the entire inner wall. Product collection bag 33 is extended adjacent to both the upper and lower portions of the inner wall and is shaped by the contour of central chamber 2's inner wall during centrifugation. The inner wall of the central chamber has a varying radius with respect to the central axis of rotation 100 shaped either by an insert 71, 81, 91, 201 or 301 shown in FIGS. 2, 3, 4, 56 or by the use of the central chamber inner wall 171 of FIG. 7. The product collection bag is shaped by the centrifugal force to conform to the shape of the inner wall of the central chamber 2. Thus, the radius of the product collection bag is also varied by the shaping. When subjected to the centrifugal force, the platelets will form a layer farthest from the central axis of rotation 100 due to their sedimentation velocity. Decreasing or increasing the inner wall radius of the central chamber from top to bottom of the chamber either by manufacture 171 as shown in FIG. 7 or by using an insert 71, 81, 91, 201 or 301 in FIG. 2, 3, 4, 5 or 6 reduces surface area for the platelets to form a layer by preventing the platelets from contacting the entire inner wall.

As shown in FIGS. 2, 3, 4, 5 and 6, adding an insert 71, 81, 91, 201 or 301 or using of the central chamber inner wall 171 of FIG. 7 to vary the radius of the central chamber between the central axis of rotation 100 and the inner wall permits the platelets to pack or sediment out along the portion of the wall with the greatest radius, including upper portions 76, 86, 96, 206 or 176 of the inner wall or, alternatively, the lower portion 307 of the inner wall. This is because the platelets will sediment out faster than any remaining less dense plasma or diluting fluid. The denser platelets under centrifugal force that have been expressed tend to move to form a layer farthest from the rotation axis. If the layer forms only in the upper portions 76, 86, 96, and 206 or, alternatively, the lower portion 307, of the inner wall, there will be fewer numbers of platelets contacting the surface area of the bag 33 than if the platelet layer extended along the entire height of the bag parallel to the central axis of rotation 100, as in the prior art FIG. 1.

Platelets in plasma have a lower sedimentation velocity generally than platelets that are stored in a platelet additive solution (PAS). Generally, platelets in such an additive solution have a higher sedimentation velocity and thus may be more likely to form a film on the bag wall over its height. Thus, using the configurations of FIGS. 2, 3, 4, 5, 6 and 7 reduce the ability of platelets in PAS to form such a film.

The invention claimed is:

1. A centrifuge for processing buffy coat comprising:
    a rotor having a central axis of rotation;
    a central chamber on the rotor capable of receiving a product collection bag, the central chamber comprising an inner wall;
    an insert configured to fit within the central chamber and to vary a radius of the inner wall of the central chamber, the insert comprising:
        a top side;
        a bottom, wherein the insert has a height between the top side and bottom, the height being less than the height of the central chamber;
        an outer side; and
        an inner side having a varying radius from the central axis of rotation;
    wherein the inner side defines a portion of the inner wall of the central chamber, the inner wall of the central chamber comprising:
        an upper portion, wherein the upper portion is above the insert, and a lower portion, wherein, when the product collection bag is received in the central chamber, the bag extends adjacent to both the upper and lower portions of the inner wall;

a separation chamber capable of receiving a separation vessel containing buffy coat and connected to the product collection bag wherein separated buffy coat components can pass from the separation chamber to the central chamber.

2. The centrifuge according to claim 1, wherein the upper portion of the inner wall has a constant radius with respect to the central axis of rotation.

3. The centrifuge according to claim 1, wherein the upper portion of the inner wall has a greater radius than any radius of the lower portion.

4. The centrifuge according to claim 1, wherein the inner wall further comprises a middle portion that is between the upper and lower portions of the inner wall, wherein a top of the lower portion of the inner wall is defined by the middle portion of the inner wall.

5. The centrifuge according to claim 4, wherein the radius with respect to the central axis of rotation of the lower portion of the inner wall decreases from the top to the bottom.

6. The centrifuge according to claim 4, wherein the central chamber comprises an outer wall and wherein the middle portion is sloped at an angle greater than or equal to 0 degrees and less than or equal to 180 degrees with respect to the outer wall of the central chamber.

7. The centrifuge according to claim 1, wherein the separated buffy coat component is platelets, wherein the platelets are passed to the product collection bag, wherein the inner wall is configured such that the platelets sediment out along the upper portion of the inner wall.

8. The centrifuge according to claim 1, wherein the separation chamber surrounds the central chamber.

9. A system for processing buffy coat, comprising:
a bag assembly, comprising:
a separation vessel,
a product collection bag,
at least one conduit connecting the separation vessel to the product collection bag,
a centrifuge for processing buffy coat comprising:
a rotor having a central axis of rotation;
a central chamber on the rotor, wherein the product collection bag is in the central chamber, and the central chamber comprises an inner wall;
an insert configured to fit within the central chamber and to vary a radius of the inner wall of the central chamber, the insert comprising:
a top side;
a bottom, wherein the insert has a height between the top side and bottom, the height being less than the height of the central chamber;
an outer side; and
an inner side, having a varying radius from the central axis of rotation;
wherein the inner side defines a portion of the inner wall of the central chamber, the inner wall of the central chamber comprising:
an upper portion, wherein the upper portion is above the insert; and
a lower portion, wherein the product collection bag extends adjacent to both the upper and lower portions of the inner wall;
a separation chamber capable of receiving the separation vessel containing buffy coat.

10. The system according to claim 9, wherein the upper portion of the inner wall has a constant radius with respect to the central axis of rotation.

11. The system according to claim 9, wherein the upper portion of the inner wall has a greater radius than any radius of the lower portion.

12. The system according to claim 9, wherein the inner wall further comprises a middle portion that is between the upper and lower portions of the inner wall, wherein a top of the lower portion of the inner wall is defined by the middle portion of the inner wall.

13. The system according to claim 12, wherein the radius with respect to the axis of rotation of the lower portion of the inner wall decreases from the top to the bottom.

14. The system according to claim 12, wherein the central chamber comprises an outer wall and wherein the middle portion is sloped at an angle greater than or equal to 0 degrees and less than or equal to 180 degrees with respect to the outer wall of the central chamber.

15. The system according to claim 9, wherein the separated buffy coat component is platelets, wherein the platelets are passed to the product collection bag, wherein the inner wall is configured such that the platelets sediment out along the upper portion of the inner wall.

16. The system according to claim 9, wherein the separation chamber surrounds the central chamber.

* * * * *